US010920186B2

(12) United States Patent
Nelissen et al.

(10) Patent No.: US 10,920,186 B2
(45) Date of Patent: Feb. 16, 2021

(54) DEVICE FOR CULTURING CELLS

(71) Applicant: Greiner Bio-One GmbH, Frickenhausen (DE)

(72) Inventors: Franciscus Petrus Nicolaas Nelissen, Venray (NL); Antoon Van Beek, Almere (NL)

(73) Assignee: GREINER BIO-ONE GMBH, Frickenhausen (DE)

( * ) Notice: Subject to any disclaimer, the term of this patent is extended or adjusted under 35 U.S.C. 154(b) by 98 days.

(21) Appl. No.: 14/356,526

(22) PCT Filed: Nov. 7, 2012

(86) PCT No.: PCT/NL2012/050783
§ 371 (c)(1),
(2) Date: May 6, 2014

(87) PCT Pub. No.: WO2013/070073
PCT Pub. Date: May 16, 2013

(65) Prior Publication Data
US 2014/0349392 A1    Nov. 27, 2014

(30) Foreign Application Priority Data

Nov. 7, 2011 (NL) ...................................... 2007734

(51) Int. Cl.
*C12M 1/00* (2006.01)
*C12M 1/12* (2006.01)
*C12M 1/24* (2006.01)

(52) U.S. Cl.
CPC ............ *C12M 29/10* (2013.01); *C12M 23/08* (2013.01); *C12M 25/06* (2013.01)

(58) Field of Classification Search
CPC ...... C12M 23/44; C12M 25/06; C12M 23/08; C12M 29/10
(Continued)

(56) References Cited

U.S. PATENT DOCUMENTS 3,152,988 A * 10/1964 Gutkowski ............ B01D 29/46
210/486
4,201,845 A * 5/1980 Feder ...................... C12M 23/12
435/297.2
(Continued)

FOREIGN PATENT DOCUMENTS

CN       1381561 A        11/2002
EP       0402272 A2 *     12/1990 ............ C12M 29/16
(Continued)

OTHER PUBLICATIONS

Chinese Office Action for Correspondending CN Application No. 201280066260.8, dated Aug. 9, 2016, 9 Pages.

*Primary Examiner* — Liban M Hassan
(74) *Attorney, Agent, or Firm* — Casimir Jones, S.C.; Tanya Arenson

(57) ABSTRACT

The invention relates to a device for culturing cells, which device comprises a bottom wall, at least one side wall as well an upper wall for forming an interior volume that can be shut off from the outside world, a liquid culture comprising cells being present on the bottom wall in use, between the at least one side wall, to which volume fluid can be supplied via at least one supply channel disposed in the upper wall and from which fluid can be discharged via at least one discharge channel disposed in the upper wall.

25 Claims, 15 Drawing Sheets

(58) Field of Classification Search
USPC .............................................. 435/289.1, 325
See application file for complete search history.

(56) References Cited

U.S. PATENT DOCUMENTS

| | | | | |
|---|---|---|---|---|
| 4,377,639 | A | * | 3/1983 | Lee ........................ C12M 27/02 |
| | | | | 435/299.1 |
| 5,240,854 | A | | 8/1993 | Berry |
| 5,658,797 | A | * | 8/1997 | Bader .................... C12M 23/24 |
| | | | | 435/284.1 |
| 5,686,301 | A | * | 11/1997 | Falkenberg ............ C12M 23/24 |
| | | | | 422/552 |
| 6,465,242 | B1 | * | 10/2002 | Kanipayor ............. C12M 23/08 |
| | | | | 219/386 |
| 7,867,761 | B2 | | 1/2011 | Esser et al. |
| 2001/0055803 | A1 | | 12/2001 | Wall |
| 2005/0130254 | A1 | | 6/2005 | Park |
| 2011/0263021 | A1 | * | 10/2011 | Stobbe ................... C12M 23/34 |
| | | | | 435/398 |

FOREIGN PATENT DOCUMENTS

| | | |
|---|---|---|
| WO | 90/08816 | 8/1990 |
| WO | 03/085080 | 10/2003 |

* cited by examiner

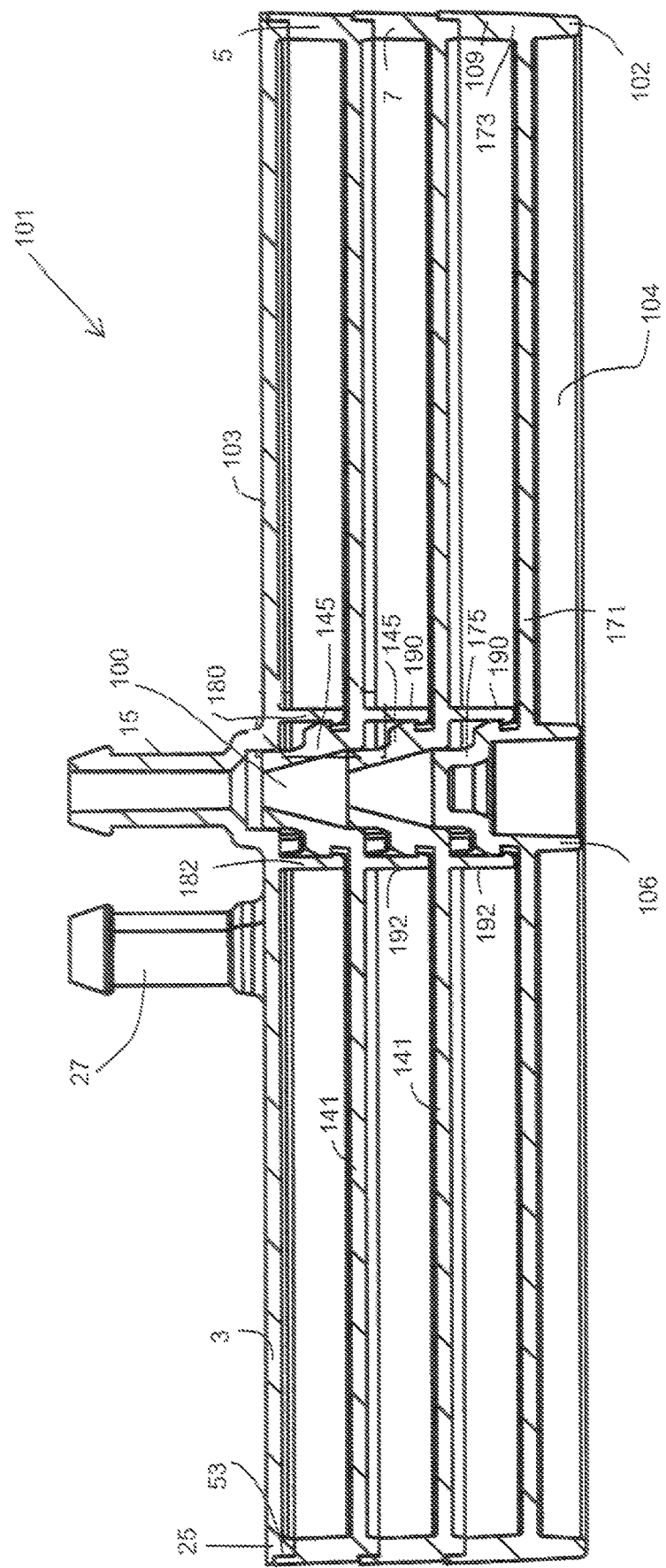

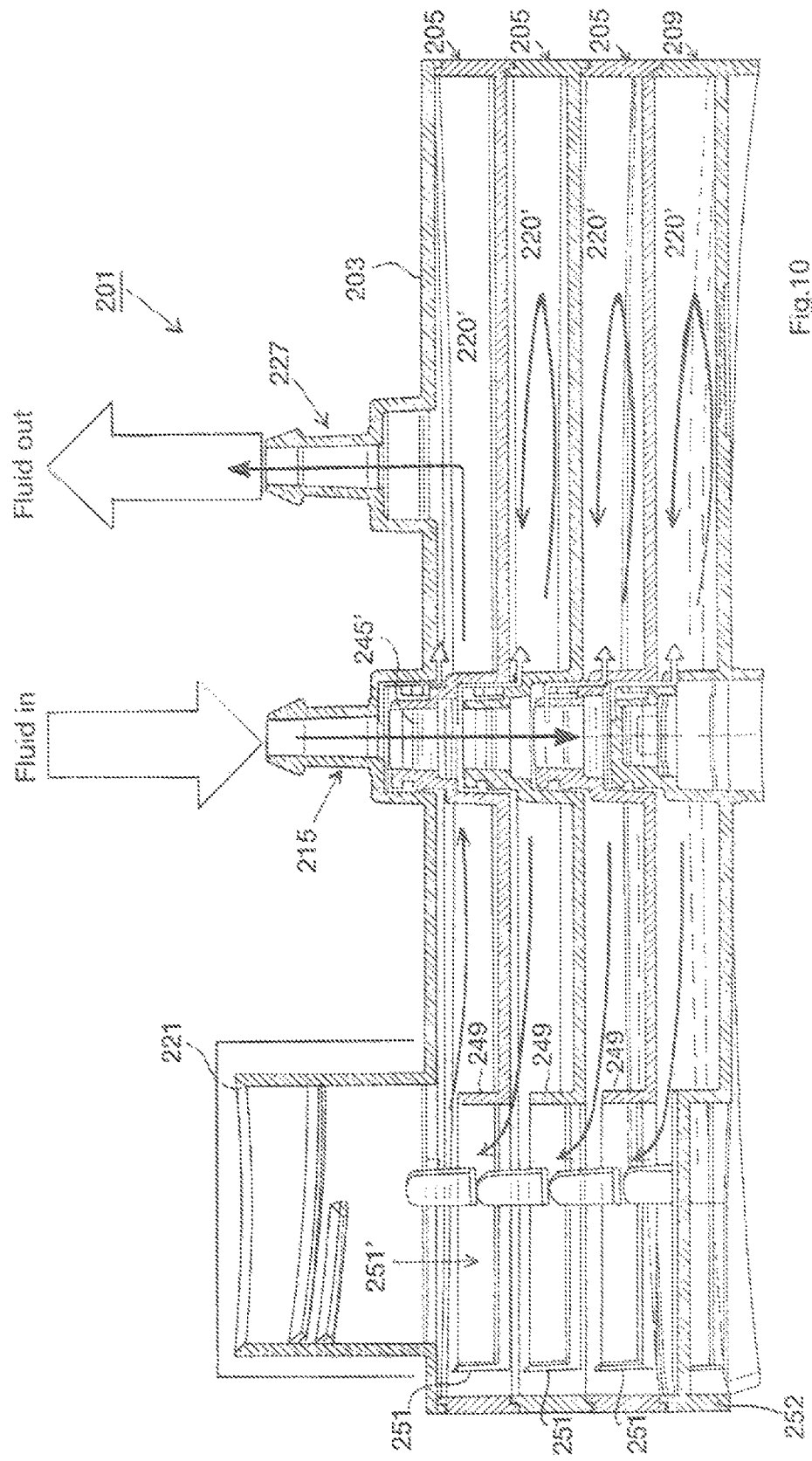

DEVICE FOR CULTURING CELLS

CROSS-REFERENCE TO RELATED APPLICATIONS

The present application is a U.S. 371 national phase entry of pending International Patent Application No. PCT/NL2012/050783, international filing date Nov. 7, 2012, which claims priority to NL2007734, filed Nov. 7, 2011, the contents of which are incorporated by reference in their entireties.

The invention relates to a device for culturing cells, which device comprises a bottom wall, at least one side wall as well as an upper wall for forming an interior volume that can be shut off from the outside world, a liquid culture comprising cells being present on the bottom wall in use, enclosed by said at least one side wall, to which volume fluid can be supplied via at least one supply channel disposed in the upper wall and from which fluid can be discharged via at least one discharge channel disposed in the upper wall.

Such a device for culturing cells is known from U.S. Pat. No. 7,867,761. The device that is known therefrom has an upper wall forming the upper side of the device as well as a bottom forming the bottom side, between which bottom and which upper wall several intermediate bottoms may be disposed. Near the circumferential edge of the upper wall, the upper wall is provided with a first supply channel extending towards the bottom and also with a second discharge channel extending from the upper wall to the bottom, which discharge channel is disposed on the other side, opposite the first supply channel.

A drawback of a device thus configured is that the gases, such as oxygen, that are needed for the culture cannot be optimally distributed over the culture area.

Accordingly it is an object of the present invention to provide a device in which fluid being supplied can be distributed better over the culture area.

This object is achieved with the device according to the present invention in that the upper wall is provided with a centrally disposed supply channel for supplying fluid into the interior volume, wherein the centrally disposed supply channel is spaced from the central axis of the device by a distance which is smaller than half the smallest distance between the central axis and the at least one side wall. The supply channel preferably extends through the interior from the upper wall, at right angles to the bottom wall.

As a result of the central position of the supply channel relative to the culture, the fluid being supplied via the supply channel, normally a gas, can be distributed better and more evenly over the entire culture area. A better distribution of the fluid comprising gaseous oxygen or nutrients, for example, over the area of the culture will be conducive to the growth of the cells in the culture. The more centrally the supply channel is disposed in the upper wall relative to the central axis of the device, the more centrally the fluid being supplied will be distributed over the area of the culture. Consequently, the central axis of the device preferably coincides with the central axis of the supply channel.

The device is preferably cylindrical in shape, so that the device comprises only one cylindrical side wall. In the case of a cylindrical shape, the centrally disposed supply channel functions as a kind of point source, which distributes the fluid evenly in all directions over the culture area in the direction of the side wall of the cylindrical device.

It is also possible, however, to use the central position of the supply channel according to the invention as described above in a device having a configuration that comprises corners, so that the device comprises several side walls arranged at an angle relative to each other.

In one embodiment of the device according to the invention, the upper wall is a cover, whilst the bottom wall is provided with a bottom connecting part that can in part be connected to, preferably in, a supply channel opening of the supply channel of the upper wall configured as a cover, wherein the bottom connecting part comprises at least one feed-through aperture for allowing fluid to pass into the interior in a connected condition. Such a cover has the advantage that the culture material can be easily placed in the device, after which the cover can be attached/connected to the rest of the device by means of the bottom connecting part, so that a closed unit can be formed.

In yet another embodiment of the invention, at least one intermediate bottom with at least one intermediate side wall is provided between the bottom wall and the upper wall, providing at least one intermediate space, in which intermediate space another liquid culture with cells may be present on the intermediate bottom in use, enclosed by the at least one intermediate side wall, wherein said at least one intermediate bottom is provided with a passage connected to the supply channel, which passage forms a passageway for fluid in the direction of the bottom wall and which comprises at least one feed-through aperture for supplying fluid from the passageway into the intermediate space. The intermediate space thus forms a subvolume of the internal volume of the device.

In this way a device can be provided which is made up of several levels. On the intermediate bottom of each level a culture may be present, which is in contact with a culture of another level, not directly but via a passage channel (defined hereinafter), wherein each level can be provided with fresh fluid by means of the centrally disposed passageway. In this way a device comprising as many as 250 levels can be provided.

Preferably at most two, preferably only one, feed-through aperture(s) are provided for each level.

Preferably, at most two, preferably exactly one, feed-through aperture(s) are provided in the passageway to a subvolume. The at most two, preferably one, feed-through aperture enables the fluid to flow evenly from the passageway into a subvolume and be distributed evenly and with a minimum of turbulence therein.

The preceding aspect can also be used independently of the main concept of the present invention, and be protected as such, in a device for culturing cells, which comprises a bottom wall, at least one side wall as well as an upper wall for forming an interior volume that can be shut off from the outside world, with a liquid culture comprising cells being present on the bottom wall in use, enclosed by said at least one side wall, to which volume fluid can be supplied via at least one supply channel disposed in the upper wall and from which fluid can be discharged via at least one discharge channel disposed in the upper wall, wherein at least one intermediate bottom with at least one intermediate side wall is provided between the bottom wall and the upper wall, providing at least one intermediate space, in which intermediate space a further liquid culture may be present on the intermediate bottom is use, enclosed by said at least one intermediate side wall, wherein said at least one intermediate bottom is provided with a passage connected to the supply channel, which passage forms a passageway for fluid in the direction of the bottom wall and which comprises at most two, preferably exactly one, feed-through aperture(s) for supplying fluid feed-through into the intermediate space.

Preferably, said one or two feed-through apertures is/are located on the side remote from the passage channel of a passage wall defining the passageway. In an embodiment comprising exactly one passage, said one feed-through aperture may in that case be located in line with the imaginary line through the central axes of the passage channel and the passageway. The fluid will thus flow away from the passage into the intermediate space or the subvolume. Because the fluid must eventually exit the intermediate space or the subvolume through the passage channel, the fluid is thus properly distributed over the intermediate space. Thus, the entire culture present in an intermediate space is reached by fluid flowing from the feed-through aperture. In an embodiment comprising two feed-through apertures, the two feed-through apertures are preferably located in the part of the passage wall remote from the passage channel, preferably on either side thereof, evenly spaced from the point of said passage wall that is intersected by the extension of the imaginary line through the central axes of the passage channel and the passageway.

The device may be in one part, which means that the side walls and intermediate side wall(s) form one whole, possibly of non-detachably interconnected (intermediate) side walls, with the bottom wall, the intermediate bottom(s) and the upper wall.

In another embodiment of the invention, the at least one intermediate bottom can be detachably connected to another intermediate side wall or to the side wall by means of a connecting mechanism.

In this way it is also possible to provide a device comprising several levels. The additional advantage is that the number of levels can be adjusted by an operator or even mechanically before the device is placed into service. Using the connecting mechanism, a user-friendly device which can be assembled by an operator himself is provided.

The term "connecting mechanism" as used herein is a collective term for various parts of the device. Examples of such parts will be discussed one by one hereinafter; they can be used in combination with each other but also separate from each other in the device according to the present invention.

The connecting mechanism may be made up of an end portion of the bottom connecting part as well as an end portion of the passage of the at least one intermediate bottom, wherein each end portion is configured so that it can be connected in a supply channel opening of the supply channel of the upper wall or in an passage aperture of the passageway, wherein each end portion or the supply channel opening or the passage aperture is provided with at most two feed-through apertures through which fluid can be supplied to each culture in the device in a connected condition.

In this way this part of the connecting mechanism connects the cover, the intermediate bottom(s) and the bottom walls, and a supply of fresh fluid to the subvolumes is ensured by means of the feed-through apertures. In this way two functions, viz. providing a mechanical connection and providing a fluid supply to every level are combined in the connecting mechanism.

The shape, the number and the dimensions of the feed-through apertures will eventually determine how the fluid will be distributed over the culture area. Depending on the dimensions and the shape of the device, and possibly also the culture material to be placed therein, these properties of the apertures can be determined by experiment. Preferably, each end portion comprises one, at most two, feed-through aperture(s) that function(s) to supply fluid from the passageway to a specific culture.

The connecting mechanism is further provided with a stepped upper edge of the side wall and/or the intermediate side wall remote from the bottom wall or the intermediate bottom as well as with a complementarily stepped upper wall edge of the upper wall and/or with a complementarily stepped edge of the intermediate bottom.

The connecting mechanism comprises a special configuration of the edges such that the side walls form of fluid-tight connection together with the cover and/or the intermediate bottom, so that the culture or the cultures at the various levels are shut off from the outside world in use.

The connecting mechanism is further provided with a snap mechanism comprising at least one cam and at least one notch in the upper wall edge and/or the edge of the intermediate bottom and also in the upper edge of the at least one side wall and/or intermediate side wall.

By means of the downwardly extending cam on the cover edge, for example, the cover can be snapped in place in the notch which is provided in the upper edge of the side wall, for example. The notch may also be provided in the cover edge, and the cam, which will extend upwards in that case, may be provided in the upper edge. In addition, the cam-notch connection ensures that all the parts in the cover, in particular the supply channel with the bottom connecting part, are correctly aligned with other parts in the device. Such another part may be a decentrally disposed inlet opening for culture liquid, which is spaced from the central axis by a distance which is preferably larger than half the smallest distance between the central axis and the at least one side wall. The decentral inlet opening is located closer to the side walls than the supply channel, therefore. The decentral inlet opening must be correctly aligned with a passage opening in the intermediate bottom, for example for filling the device with culture liquid, which can be achieved in a user-friendly and simple manner by means of the above-described snap mechanism. Another part that is provided in the cover is a discharge channel. The inlet opening, the supply channel as well as the discharge channel preferably lie in a virtual plane transversely to the upper wall in the cover.

The connecting mechanism may furthermore be provided with at least two fingers pointing in the direction of the bottom wall, which fingers are each attached with a first end thereof to the side of the upper wall and/or the intermediate bottom that faces the bottom wall, and which are arranged around the passageway formed by the supply channel, the passage and the bottom connecting part. In the connected condition, the second ends of the fingers are fixed in recesses which are preferably provided in the bottom connecting part and/for the passage.

By means of said snap mechanism comprising the fingers and the recesses, the various parts of the device can be reliably connected together.

Furthermore, a part of the bottom connecting part and the at least one passage under the end portion of the bottom connecting part is conical in shape, which conical part is further provided with radially extending flanges.

Such a configuration provides a solid connection with the cover as well as with the intermediate bottom, with the underside of the cover or the intermediate bottom moreover being firmly centrally supported by means of the flanges.

The connecting together of stacked parts of the device may also take place by means of an elastic sealing ring. In addition to providing a good seal, the elastic ring can also provide a clamped connection or a friction connection between part of a channel, such as the passageway and/or the passage channel, that are moving, or at least have been moved, one into the other.

For filling the device according to the invention with culture material, the upper wall may be provided, as already mentioned above, with at least one inlet and/or outlet opening separate from the supply channel and the discharge channel in addition to the supply channel and the discharge channel for supplying and/or discharging culture material to and from, respectively, the interior. By means of the above-described snap mechanism comprising the cam and a notch, a correct alignment can be ensured in a simple manner. The inlet and/or outlet opening in the cover may be shut off from the outside world by means of a screw cap, for example. To fill the device according to the present invention with culture material, the at least one inlet and/or outlet opening can be opened and material can be introduced into the device through said opening. Following that, the at least one inlet and/or outlet opening can be closed, for example by means of the screw cap, and the device is placed on a side formed by the side wall and the intermediate side walls, with the inlet and/or outlet opening in the lowermost position. According to the law of communicating vessels, the liquid will now spread evenly over all levels. By rotating the device at least one quarter turn about its central axis, the at least one inlet and/or outlet opening will be moved to a higher position, as a result of which the culture material will no longer spread further over the various subvolumes of the levels and the device can be tilted back in its entirety from the situation in which the side is positioned on a supporting surface to a situation in which the bottom is positioned on said supporting surface. In this operating position of the device, the culture process can start. As a result of the provision of the at least one inlet and/or outlet opening or, in other words, the passage opening, separate from the supply channel and the discharge channel it is possible, however, for a supply or discharge hose to remain (semi) permanently connected to the at least one inlet and/or outlet opening. Through said hose, culture liquid can be supplied via the passage channel for starting a culture, which culture liquid will be distributed over the subvolumes. After a culture cycle, the culture liquid with the cultures can subsequently be removed from the device through the at least one inlet and/or outlet opening. In spite of the (semi-) permanent connection, fluid can be supplied to the culture process through the supply channel and through the discharge channel. During the period between the supplying and discharging of culture liquid, the passage channel is free from culture liquid, thus enabling communication between the subvolumes; during culturing, the passage channel can be used for carrying fluid from the subvolumes, via the passage channel, to the uppermost subspace under the cover provided with the discharge channel. This process takes place automatically when fluid is introduced into the device under pressure through the supply channel, because thus a relative overpressure will be generated in the interior, which is in communication with the discharge channel via the passage channel.

The above aspects can also be implemented and protected independently of the main concept of the present invention as a device for culturing cells, which device comprises a bottom wall, at least one side wall as well as an upper wall for forming an interior volume that can be shut off from the outside world, a liquid culture comprising cells being present on the bottom wall in use, enclosed by said at least one side wall, to which volume fluid can be supplied via at least one supply channel disposed in the upper wall and from which fluid can be discharged via at least one discharge channel disposed in the upper wall, wherein the upper wall is provided with at least one inlet and/or outlet opening or, in other words, passage opening, separate from the supply channel and the discharge channel in addition to the supply channel and the discharge channel for supplying and/or discharging culture material to and from, respectively, the interior. Also in this case it applies that the distribution of fluid being supplied through the supply channel will take place less optimally within the subvolumes in the case of a decentral location of the supply channel and thus the passageway, but the advantage that the supply and discharge holes need not be connected and disconnected all the time is achieved in this way, however.

Preferably, the at least one passage opening is disposed decentrally relative to the upper wall, with the decentrally disposed passage opening preferably being spaced from the central axis of the device by a distance larger than half the smallest distance between the central axis and the at least one side wall. When the at least one passage opening is located near the side wall of the device, furthermore preferably has a common tangent with an (intermediate) side wall, the culture liquid can be distributed evenly over the subvolumes or be removed from the subvolumes in a simple manner via the passage channel and the at least one passage opening. The entire device can to that end be tilted, preferably through 90 degrees. It is preferable, therefore, if the at least one passage opening is located near the side wall of the device.

Using the connecting mechanism which connects the intermediate bottoms together and to the bottom and the cover and which further provides a fluid-tight connection for preserving the contents of the device from the atmosphere, a centrally disposed fluid channel is moreover provided, by means of which the culture areas arranged above each other are uniformly provided with fluid. Preferably, the central axes of the inlet opening, the supply channel as well as the discharge channel lie in a virtual plane, which virtual plane extends transversely to the upper wall.

In a preferred embodiment of the present invention, a passage opening is provided in said one or more intermediate bottoms, which passage openings are substantially aligned with an inlet and/or outlet opening in the upper wall so as to form a passage channel for culture liquid.

It is preferable in that regard if a passage opening is bounded by an intermediate wall extending perpendicularly to the intermediate bottom wall, such that the passage channel is in communication with the respective interior space. When the passage channel is not being used for supplying or discharging culture liquid, it can thus be utilised for allowing fluid being supplied through the supply channel to flow from the subvolumes in the direction of the uppermost subvolume present below the upper wall provided with the discharge channel. Subsequently, the fluid can be discharged from the device via the discharge channel.

It is preferable in that regard if the proportion between the cross-section of the passage channel and that of the passageway is greater than 2:1, preferably greater than 5:1. The fluid is introduced into the device under pressure via the supply channel. If the diameter of the passage channel is larger than that of the passageway, the pressure in the passage channel will be lower, at least in the case of a sufficient discharge of fluid through the discharge channel, so that fluid can flow out of the passageway into the subvolumes and from the subvolumes to the passage channel in a relatively simple manner.

The above aspects can be implemented and protected independently of the main concept of the present invention as a device for culturing cells, which device comprises a bottom wall, at least one side wall as well as an upper wall for forming an interior volume that can be shut off from the outside world, a liquid culture comprising cells being present on the bottom wall in use, enclosed by said at least one side wall, to which volume fluid can be supplied via at least one supply channel disposed in the upper wall and from which fluid can be discharged via at least one discharge channel disposed in the upper wall, wherein two or more intermediate bottoms with a passage opening are provided, which passage openings are substantially aligned with an inlet and/or outlet opening in the upper wall so as to form a passage channel for culture liquid in a simple manner, wherein the proportion between the cross-section of the passage channel and that of the passageway is greater than 2:1, preferably greater than 5:1. The fluid is introduced into the device under pressure via the supply channel. If the diameter of the passage channel is larger than that of the passageway, the pressure in the passageway can be higher than in the passage channel, so that fluid will flow relatively easily from the passageway to the passage channel via the subvolumes in use. Ideally, the passage channel has a relatively large diameter, because the passage channel is used not only for, preferably gaseous, fluid but also for the supply and discharge of culture material in the form of liquid.

In a preferred embodiment of the present invention, the bottom wall is provided with at least one sensor cavity for a sensor. Thus it is possible to detect the situation in the lowermost subvolume by means of a sensor that can be mounted under the device without any, or at least with a reduced, risk of damage.

A device according to the present invention which has a cylindrical conflagration contributes to an even distribution of fluid over the subvolumes, because the maximum spacing between the passageway and the side wall of the device is substantially constant, in particular if the inlet opening and the passageway are provided on or near the central axis of the cylinder.

In a device comprising stacked subvolumes, it is preferable for the passage to be hollow so as to provide a passageway in a connected condition, wherein the bottom connecting part has an upper side which, in a connected condition, forms the end point of a passageway. In this way a passageway is formed in a simple manner by stacking.

The height of an intermediate side wall preferably ranges between 4-10 mm. The height of an intermediate side wall is furthermore preferably at least 6 mm. Furthermore preferably, the height of an intermediate side wall is at most 8 mm. The height of an intermediate side wall is the same as the spacing between two adjacent (intermediate) bottoms. The known devices as described in the introduction have an intermediate side wall having a height of more than 10 mm. The lower intermediate side walls of the level elements render the device more compact, especially if the device comprises 25, 50 or even more than 100 levels, which is not unusual. The above aspects can be implemented and protected independently of the main concept of the present invention as a device for culturing cells, which device comprises a bottom wall, at least one side wall as well as an upper wall for forming an interior volume that can be shut off from the outside world, a liquid culture comprising cells being present on the bottom wall in use, enclosed by said at least one side wall, to which volume fluid can be supplied via at least one supply channel disposed in the upper wall and from which fluid can be discharged via at least one discharge channel disposed in the upper wall, wherein two or more intermediate bottoms each having an intermediate side wall are provided, wherein the height of an intermediate side wall ranges between 4-10 mm. Put differently, wherein the spacing between two adjacent (intermediate) bottoms ranges between 4-10 mm. In this case, too, it is preferable if the spacing in question is at least 6 mm and/or at most 8 mm.

The invention further relates to a perfusion system comprising a device as described in the foregoing, which is additionally provided with an internal supply line for supplying liquid to the interior of the device and with an internal discharge line spaced from the supply line for discharging liquid from the interior of the device, wherein the supply line as well as the discharge line in the bottom wall can be connected to a supply reservoir and an outlet, respectively, of the perfusion system by means of hoses.

The invention will now be described in more detail with reference to an embodiment shown in the appended figures.

FIG. 3b is a sectional view of the level element of the device of FIGS. 1 and 3a;

FIG. 4b is a sectional view of the bottom part of the device of FIGS. 1 and 4a;

FIG. 7b is a sectional view of the further alternative embodiment of the device according to the present invention shown in FIG. 7a;

FIG. 8b is a sectional view of the level element of FIG. 8a;

FIG. 8c is a perspective view of a passage of the level element of FIG. 8a;

FIG. 9b is a sectional view of the bottom part of FIG. 9a;

FIG. 9c is a perspective view of a passage of the bottom part of FIG. 9a;

FIG. 10 is a vertical sectional view of an assembly of a bottom part and three level elements of the present invention and an associated cover.

Like parts are indicated by the same numerals in the various figures.

Figure 1:
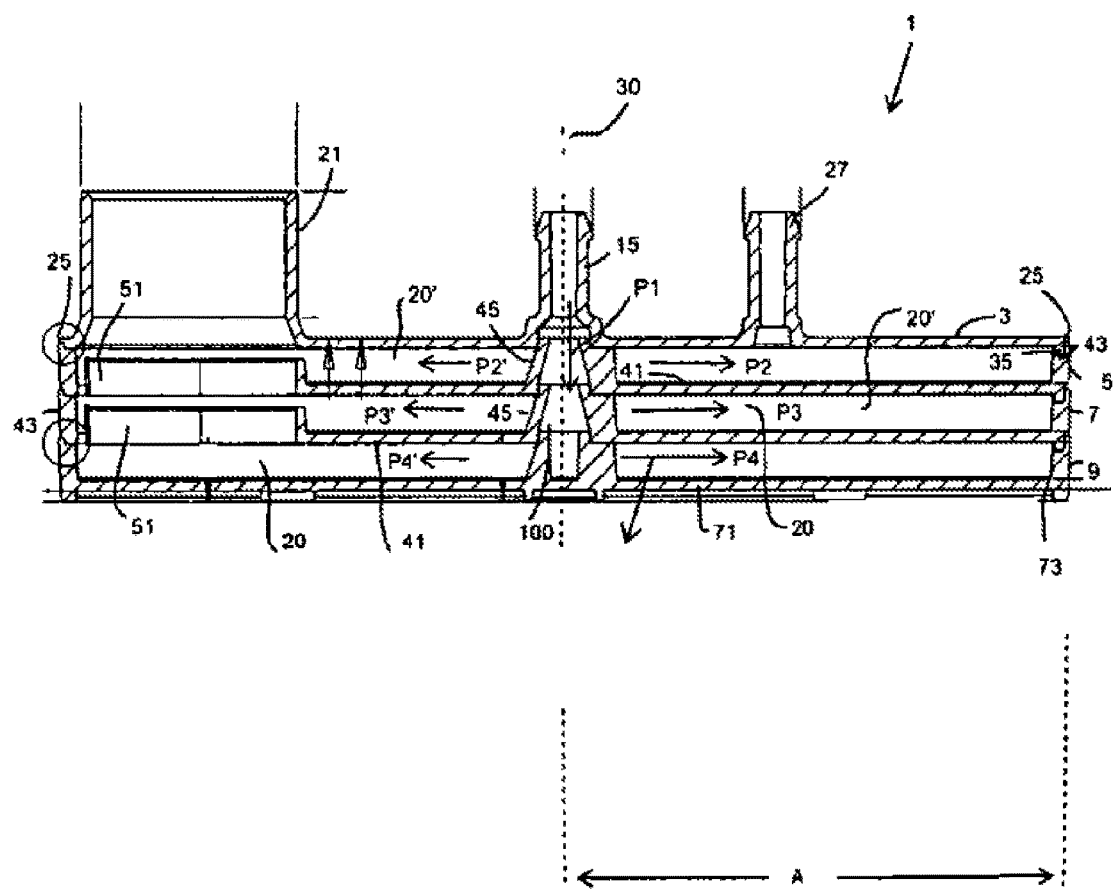
FIG. 1 is a sectional view of a device according to the present invention.

FIG. 1 shows a device 1 according to the present invention for culturing cells, said device in the illustrated embodiment being built up of an upper wall configured as a cover 3, a first level element 5, a second level element 7 as well as a bottom part 9, which are interconnected by means of a connecting mechanism comprising several parts yet to be specified hereinafter.

Figure 2A:
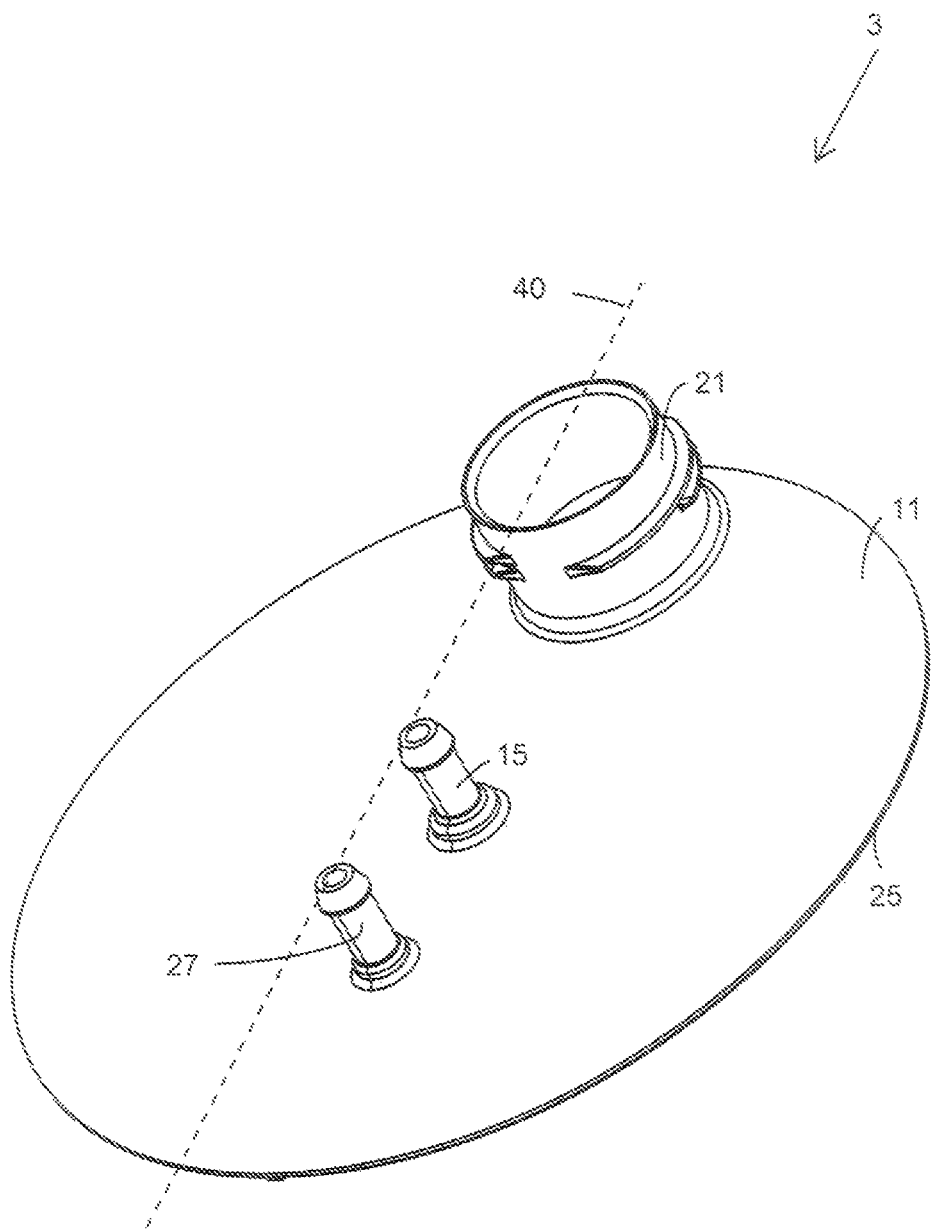
FIG. 2a is a perspective view of a cover of the device of FIG. 1.
Figure 2B:
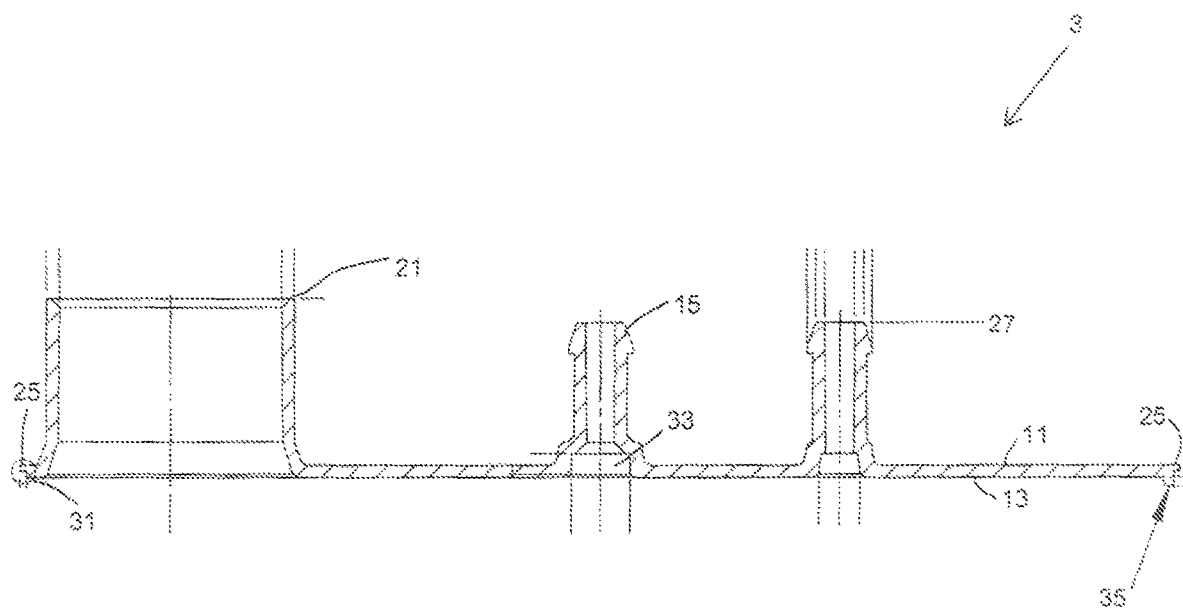
FIG. 2b is a sectional view of the cover of FIG. 1.

FIGS. 2*a*, 2*b* show in perspective view and in sectional view, respectively, a cover 3 of the device 1 of FIG. 1. The circular cover 3 has an upper cover surface 11, as well as a lower cover surface 13. The cover 3 is provided with a centrally disposed supply channel 15 for supplying fluid to the interior 20 of the device (see FIG. 1). In the device 1, the supply channel 15 that is centrally disposed in the cover 3 is spaced from the central axis 30 of the device 1 by a distance smaller than half the smallest distance A (see FIG. 1) between the central axis 30 and the at least one side wall 73; in the preferred embodiment shown in the figures, the central axis 30 of the device 1 coincides with the central axis 30 of the supply channel 15.

The cover 3 is further provided with a decentrally disposed inlet and outlet opening 21 for supplying and discharging culture material (not shown) to and from the interior 20, with the decentrally disposed inlet and outlet opening 21 being spaced from the central axis of the device 1 by a distance which is larger than half the smallest distance A between the central axis 30 and the at least one side wall 73. In the illustrated embodiment, the inlet and outlet opening 21 is located near the cover edge 25. Furthermore, a discharge channel 27 is provided between the supply channel 15 and the cover edge 25. As shown in FIG. 2*a*, the central axes of the inlet and outlet opening 21, the supply channel 15 as well as the discharge channel 27 can be intersected by a single virtual line 40 extending parallel to the cover, which line lies in a plane perpendicular to the cover 3.

In the embodiment shown in FIG. 2*b*, the connecting mechanism comprises three parts in the cover 3: a stepped (see the circle indicated at 31) cover edge 25 of the cover 3 for providing a fluid-tight connection between a side wall and the cover, a part of a snap mechanism in the form of a cam 35, as well as a specifically configured and dimensioned supply channel opening 33 of the supply channel 15.

Figure 3A:
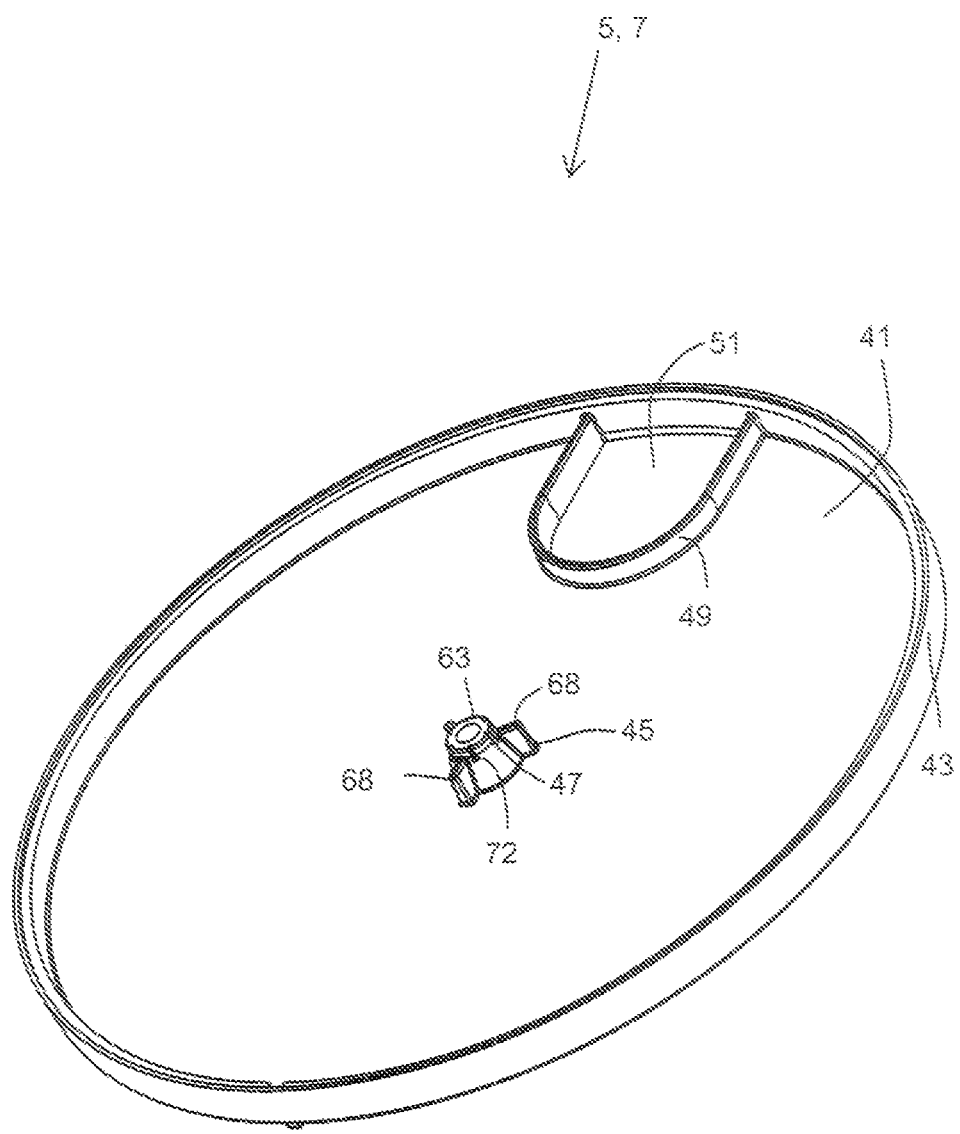
FIG. 3a is a perspective view of a level element of the device of FIG. 1.

FIGS. 3*a*, 3*b* show in perspective view and in sectional view, respectively, a level element 5, 7 of a device 1 according to the present invention. The level elements 5, 7 are practically identical to each other; the device may comprise as many as 250 level elements 5, 7. Each level element 5, 7 comprises an intermediate bottom 41 as well as an intermediate side wall 43 that extends cylindrically relative to the intermediate bottom 41, which side wall provides an intermediate space 20' of the entire interior 20. In use, a liquid culture with cells is present on the intermediate bottom, enclosed by said at least one intermediate side wall. The intermediate bottom 41 is provided with a passage 45 to be connected to the supply channel 15, which passage 45 forms a passageway for fluid in the direction of the bottom part 9 of the device 1. The passage 45 is provided with feed-through apertures 47, for supplying fluid into the intermediate space 20', also called (internal) subvolume. The feed-through apertures 47 are located in the passage 45. The connecting mechanism comprises six parts (I-VI) in the level element 5, 7:

(I) a stepped (see the circle 61 in FIG. 3*b*) intermediate upper edge 53 remote from the intermediate bottom 41 of the intermediate side wall 43,
(II) a stepped (see the circle 62 in FIG. 3*b*) transition edge 55 between the intermediate bottom 41 and the intermediate side wall 43,
(III) at least one cam 57, and
(IV) at least one recess 59, which cam 57 and which recess 59 are associated with two different snap mechanisms,
(V) a passage 45 comprising a specifically configured and dimensioned end portion 67, as well as
(VI) a specifically configured and dimensioned passage connecting opening 65.

Figure 4A:
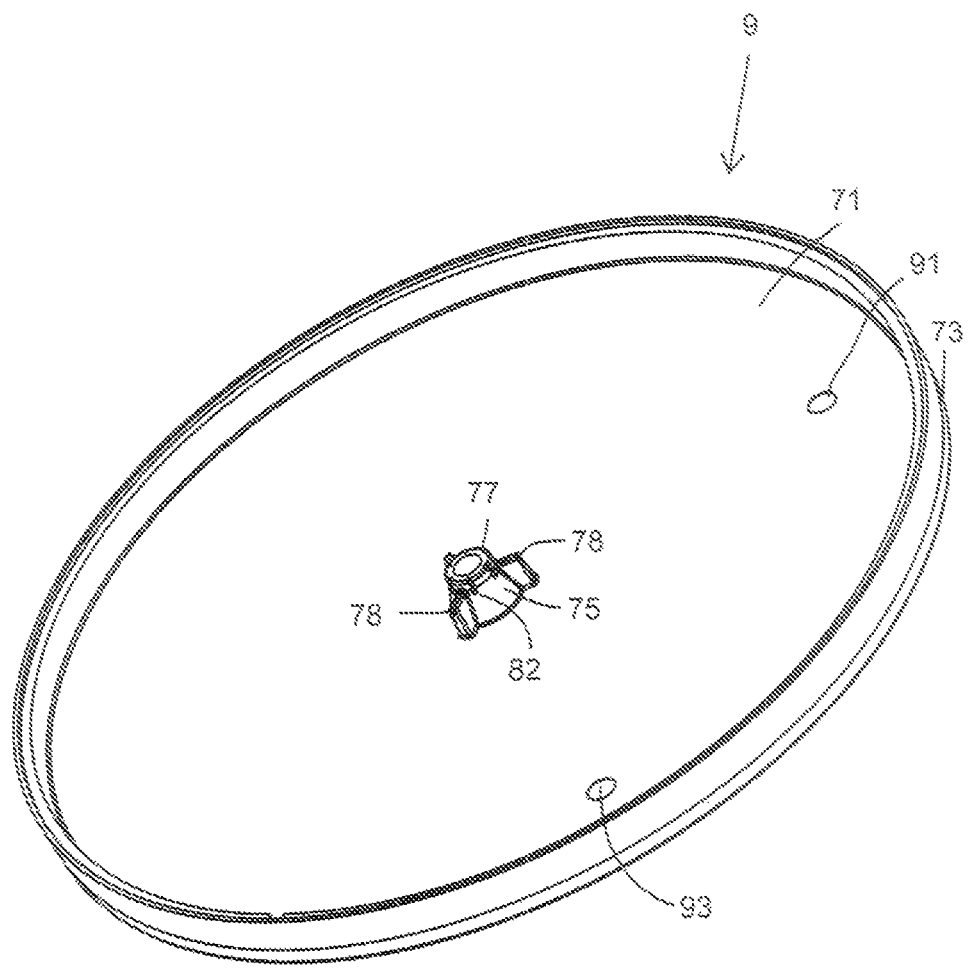
FIG. 4a is a perspective view of a bottom part of the device of FIG. 1.
Figure 4B:
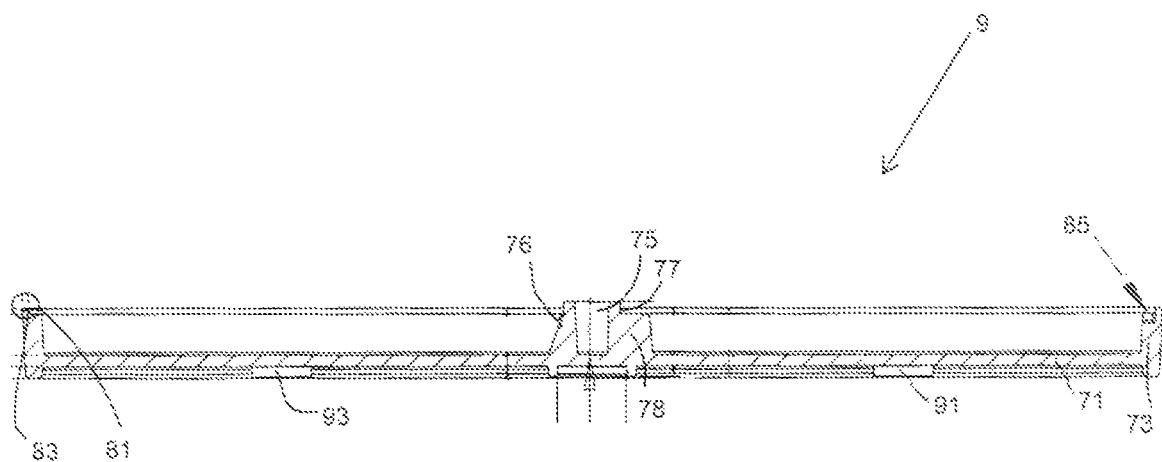

FIGS. 4*a*, 4*b* show in perspective view and in sectional view, respectively, a bottom part 9 of the device 1 according to the present invention. The bottom part 9 comprises a circular bottom wall 71, which is circumferentially provided with a side wall 73 extending transversely thereto. The side wall 73 extends cylindrically relative to the bottom wall 71. The bottom wall 71 is provided with a bottom connecting part 75, which can be connected in the supply channel opening 33 of the supply channel 15 of the cover 3 or in the (V) specifically configured and dimensioned feed-through connecting opening 65 of the passage 45 (which connection is shown in FIG. 1).

In the illustrated embodiment, the bottom connecting part 75 is configured identically to the passage 45, with this difference that the passage 45 is hollow for forming the passageway 100 in a stack of level elements 5, 7 closed by a cover 3, whilst the bottom connecting part 75 has an upper side which forms a closed bottom end of the passageway 100. Both the bottom connecting part 75 and the passage 45 have an end portion 67, 77 to be connected in the supply channel opening 33 or in the feed-through connecting opening 65 (see FIGS. 3*b* and 4*b*) as well as a conical portion 66, 76 located under the end portion 67, 77, which conical portion 66, 76 is further provided with radially extending flanges 68, 78, which support a higher part of the device 1 in the connected condition.

Each end portion 67, 77 is provided with six gap-shaped feed-through apertures 72, 82 for supplying fluid to the interior 20, which feed-through apertures are mainly located in the end portion 67, 77 and which, in the illustrated embodiment, extend minimally into the conical portion 66, 76 of the bottom connecting part of 75 and the passage 45, respectively.

The connecting mechanism comprises three parts in the bottom part 9: a stepped (see the circle 81 in FIG. 4*b*) upper edge 83 remote from the bottom wall 71 of the side wall 73, at least one part of the snap mechanism, i.e. a recess 85, as well as a specifically configured and dimensioned end portion 77 of the bottom connecting part 75.

Using the connecting mechanism of the device according to the present invention, an end user can assemble a device 1 having the desired or required number of levels himself by connecting said levels by means of parts of the connecting mechanism, whilst furthermore a fluid-tight seal between the interior 20 of the device and the outside world is ensured by means of parts of the connecting mechanism. The outer circumference of the device 1 formed by the side walls 43 of the level elements 5, 7 can be formed into an integral side wall by connecting the side walls 43 together.

In use, a supply and discharge line (not shown) is connected to the decentral inlet and outlet opening 21 for culture material. A desired amount of culture material is introduced into the device 1 via the inlet and outlet opening 21. Subsequently, the device is tilted, so that the inlet and outlet opening 21 and the passage openings 51 are located at the bottom side of the device 1. The liquid culture material is thus evenly distributed over the subvolumes. Then the device is rotated a quarter turn about its axis, so that the culture material in the various subvolumes can no longer communicate via the passageway. Then the device is tilted to an upright position again, still with the supply and discharge line connected to the inlet opening 21.

Thus, several liquid cultures with cells are present on the bottom wall 71 and the intermediate bottoms 41, enclosed by means of the side wall 73 and the intermediate walls, which cultures are separated from each other in the horizontal operating state of the device 1 that is shown in FIG. 1. Said cultures, although separated from each other, are identical to each other as regards their composition. When cells are to be cultured, special fluid prepared independently of the culture material must be supplied to the cultures. In use, fluid is supplied via the supply channel 15 in the direction indicated by arrow P1, possibly under pressure, to a passageway 100 (see FIG. 1) provided by means of the passage 45 and the bottom connecting part 75. Via the openings 72, 82 in the passage 45 and the bottom connecting part 75, respectively, the fluid is distributed over the culture surfaces in the directions indicated by arrows P2, P2', P3, P3' as well as P4, P4', so that the cells in the culture can extract the required substances from the fluid. As a result of the central position of the fluid supply channel 15 and the passages 45 relative to the cultures surfaces arranged in the form of a circle, the fluid being supplied via the supply channel 15, normally a gas, can be distributed better and more evenly over the entire area of the culture by means of the passageway 100. Such a distribution of the fluid comprising gaseous oxygen or nutrients, for example, over the surfaces of the various cultures will stimulate the growth of the cells in the culture.

The bottom wall 71 is provided with two sensor mounting holes 91, 93 (see FIGS. 4a and 4b). Preferably, a sensor (not shown) that measures the oxygen content in the culture present on the bottom wall 71 is affixed in a first mounting hole 91, whilst preferably a sensor (not shown) that measures the acidity in the culture present on the bottom wall 71 is affixed in a second mounting hole 93. Since all the cultures at all levels are identical to each other as regards their composition, and the fluid is supplied in the same manner and under the same conditions at every level, it suffices to measure only the culture present on the bottom wall 71 by means of the sensors. Said culture is representative of all the other cultures present at higher levels in the device 1.

Instead of using the two spaced-apart mounting holes 91, 93, it is also possible to provide a single hole (not shown) in which the two aforementioned sensors, or even more sensors, are located.

In use, the gases and the unused fluid are carried between the levels, via the passage openings 51, to the uppermost level element, from which they are discharged from the device 1 through the discharge channel 27.

At the end of a culture cycle, the device 1 is tilted again, so that the passageway will be located at the bottom side. Then the culture material is carried from the device through the inlet opening via the still connected supply and discharge line.

Now the differences with the views shown in FIGS. 5 and 6 of an alternative embodiment of the device 101 according to the present invention and of a detail thereof, respectively, will be discussed. Similar parts will be indicated by the same numerals as used for corresponding parts in the discussions of FIGS. 1-4b, and consequently they will not be discussed in more detail in the description of this embodiment.

The device 101 comprises a bottom part 109 which is provided with an upright edge 102 provided together with the bottom wall 171 and the side wall 173. Said cylindrical edge 102 provides a hollow space 104 in the device 101, which is open at the bottom side. On the side remote from the bottom connecting part 175, the bottom wall 171 is provided with a receiving edge 106, via which the device 101 can be connected to a drivable rotary platform.

In the alternative embodiment of the device 101 another, possibly additional snap mechanism is provided, which snap mechanism is provided with two fingers 18, 182 pointing in the direction of the bottom wall 171, which fingers are each connected via a first end thereof to the side of the cover 103 that faces the bottom wall and, for the level elements 5, 7, two fingers 190, 192 pointing in the direction of the bottom wall 171, which are each connected via a first end thereof to the side of the intermediate bottom 141 that faces the bottom wall 171. The fingers 180, 182, 190, 192 are L-shaped. A bottom connecting part 175 or a passage 145 can be positioned between two fingers 180, 182, 190, 192.

Figure 5B:
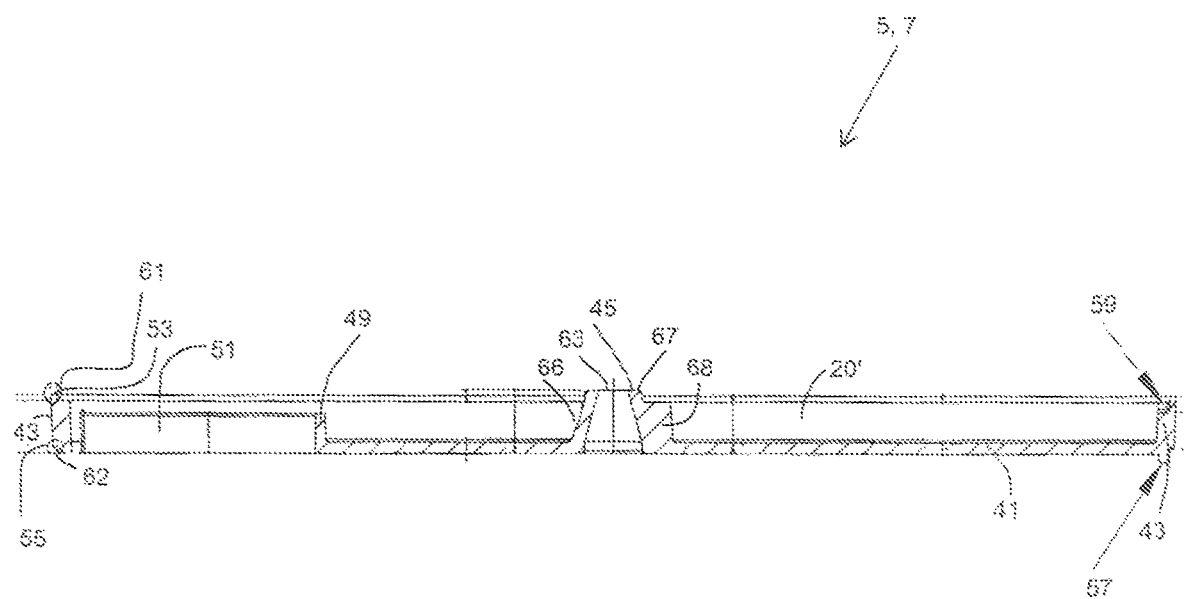
FIG. 5 is a sectional view of an alternative embodiment of a device according to the present invention.

As shown in FIG. 5, the bottom connecting part 175 does not have the same dimensions as the passage 145, but constructionally the bottom connecting part 175 has the same properties as the passage 145, which is discernible because the two are configured practically identically. FIG. 6 shows a larger-scale view of the bottom connecting part 175 that is also shown in FIG. 5. Although the bottom connecting part 175 is shown in FIG. 6, both the passage 145 and the bottom connecting part 175 comprise an end portion 177 to be explained in more detail below with reference to FIG. 6, with this difference that the passage 145 is hollow for the purpose of forming a passageway 100 (see FIG. 5), whilst the end portion 177 of the bottom connecting part 175 has an upper side 160 that forms the end of the passageway 100.

The end portion 177 comprises a cylindrical part 176 as well as an outwardly flared part 178 connecting thereto. Six feed-through apertures 172 extend from the upper side 160 of the end portion 177 to within the flared part 178. The end portions 177 of the bottom connecting part 175 and the passages 145 provide a force-locked mechanical connection between the level elements 5, 7, the bottom part 109 and the cover 103 by inserting the end portions 177 into a feed-through connecting opening or a supply channel opening. The force-locked connection is accomplished mainly by means of the outwardly flared part 178 of the end portion 177.

The feed-through apertures 172 of each end portion 177 ensure that every culture at every level is provided with the fluid being supplied via the supply channel 15 and the passageway 100.

Figure 6:
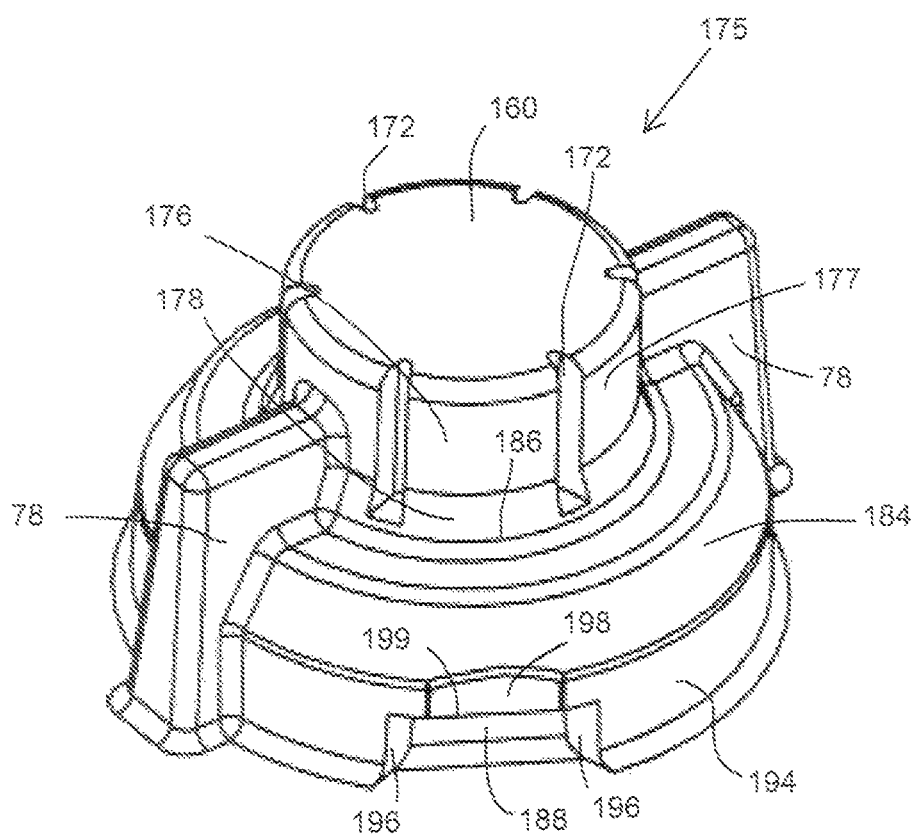
FIG. 6 is a view of a bottom connecting part of the alternative embodiment of the device according to the present invention that is shown in FIG. 5.

Like the passages 145, the bottom connecting part 175 shown in FIG. 6 further comprises a conical part 184 located under the end portion 177, which extends downwards from the edge 186 shown in FIG. 6. Two recesses 188 are present in the lower part 194 of the conical part 184, only one of which is shown in FIG. 6. Seen in the circumferential direction of the bottom connecting part 175, the recesses 188 merge into the lower part 194 of the bottom connecting part 175 via sloping surfaces 196. A hollowed-out surface 198 is provided above the recess, seen in axial direction.

The operation of the snap mechanism comprising the fingers 180, 182, 190, 192 as well as the recesses 188 is as follows. To connect the level element 7, for example, to the bottom part 109, the fingers 190, 192 of the level element 7 are elastically deformed against spring force by being pressed outward by the conical part 184 of the bottom connecting part 175, preferably, but not necessarily, by the hollowed-out surface 198. Upon further movement of the level element 7 with the fingers 190, 192 in the direction of the bottom wall 171, the fingers 190, 192 are snapped in place in the recess 188 in that the fingers 190, 192, having passed the edge 199, want to return to their original position. Seen in axial direction, the fingers 190, 192 are fixed in the recess 188 by the short part of the L-shape of the fingers 190, 192. By rotating the level element 7, the fingers 190, 192 are moved outward again against spring force from the original position by means of the sloping surfaces 196, with the fingers 190, 192 reaching the lower part 194 of the bottom connecting part 175 if the rotation is sufficiently large. By moving the level element 7 upward from the bottom wall 171 in this position of the fingers 190, 192, the fingers 190, 192 will return to their original position, with the bottom connecting part 175 being disconnected from the fingers 190, 192.

By means of said snap mechanism comprising the fingers and the recesses, the various parts of the device 101 can be reliably interconnected and be separated in a relatively simple manner, for example for cleaning the device 101.

Figure 7A:
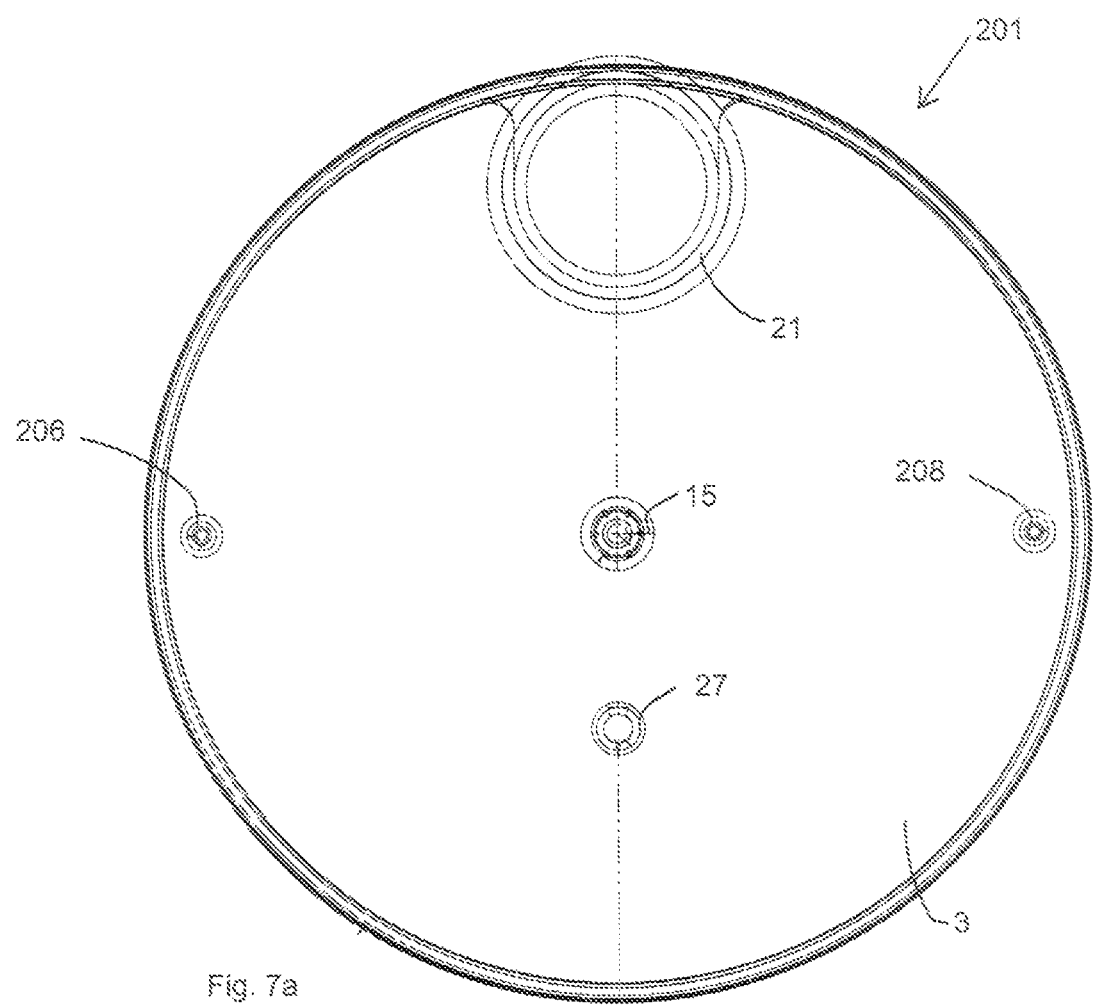
FIG. 7a is a top plan view of a further alternative embodiment of a device according to the present invention, which is suitable for use in a perfusion system.
Figure 7B:
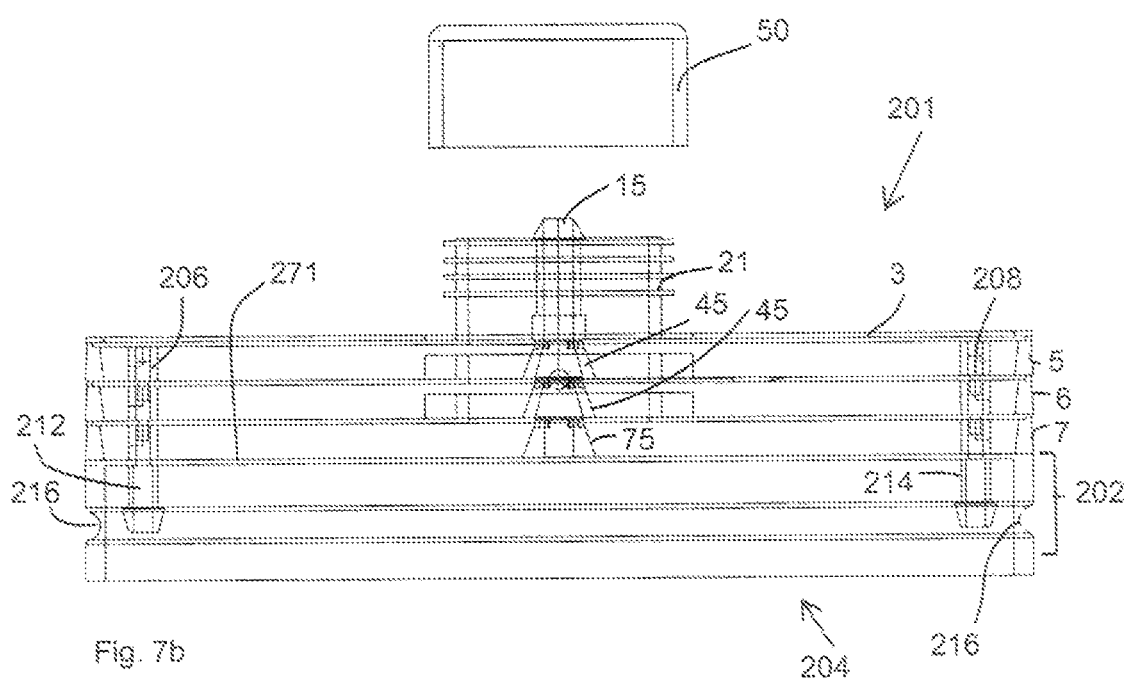

FIGS. 7a and 7b show in top plan view and in sectional view, respectively, an alternative embodiment 201 of the device according to the present invention. The device 201 is identical to the device 1, so that like parts are indicated by the same numerals without any further explanation. The device 201 is suitable for use in a perfusion system (not shown). The perfusion system comprises, inter alia, the device 201, a supply reservoir (not shown), a drain (not shown), as well as hoses. At the bottom side, the device 201 is provided with an upright edge 202, which bounds a space 204 which is open at the bottom side. At the bottom side, in the space 204, the device 201 is provided with means (not shown) by means of which the device can be easily positioned on and connected to a rotary platform (not shown). The device 201 further comprises a supply line 206 for supplying liquid to the interior of the device 201, as well as a discharge line 208 spaced from the supply line 206 for discharging liquid from the interior of the device 201, with the bottom wall 271 comprising a supply line end 212 extending into the space 204 as well as a discharge line end 214 extending into the space 204, which ends can be connected to the supply reservoir and to the drain, respectively, by means of hoses. The supply line 206 and the discharge line 208 are provided with openings at each level for supplying and discharging liquid to and from each level.

A central part of the circumferential edge 202 is provided with a cavity 216, in at least part of which a supply hose as well as a discharge hose can be positioned, which hoses can be passed into the space 204 via a hole in the edge 202, in which space the hoses are connected to the supply line end 212 and to the discharge line end 214. Motor-driven rollers (not shown), which have a dual function, extend over the parts of the hoses that are located in the cavity 216. On the one hand, the device 201 positioned on the rotary platform can be rotated by means of the rollers whilst on the other hand the pressure exerted on the hoses via the rollers provides a pump function for moving the liquid therein. In this way a peristaltic pump system is provided.

Using the perfusion system described in the foregoing, rotational kinetic cell harvesting by means of the rotary device 101 becomes possible.

It is further possible to place a hollow tube (not shown) provided with apertures in the supply line 206 or in the discharge line 208. Said tube abuts substantially without play against the inner wall of the supply line 206 or the discharge line 208. Said tube can be rotated and moved upwards and downwards from outside. The supply or discharge of liquid takes place through said hollow tube. By moving the tube in vertical direction or rotating the tube, the apertures in the tube can be aligned with the apertures in the supply line 206 or in the discharge line 208, making it possible to control the supply and discharge of liquid to a specific level by means of the tube.

Figure 8B:
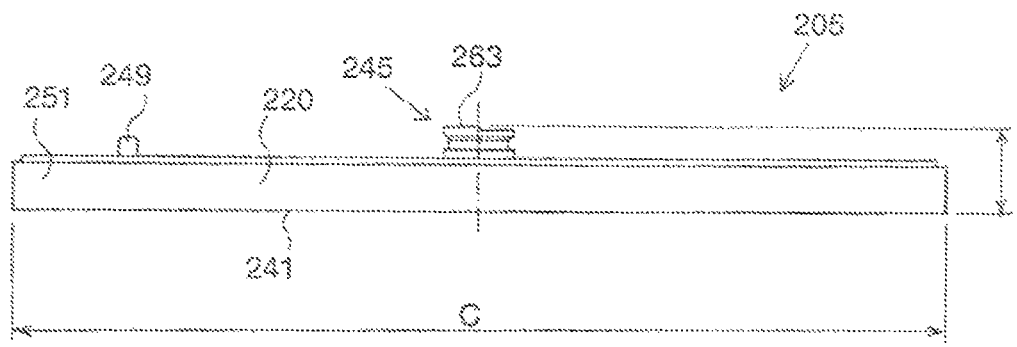
Figure 8A:
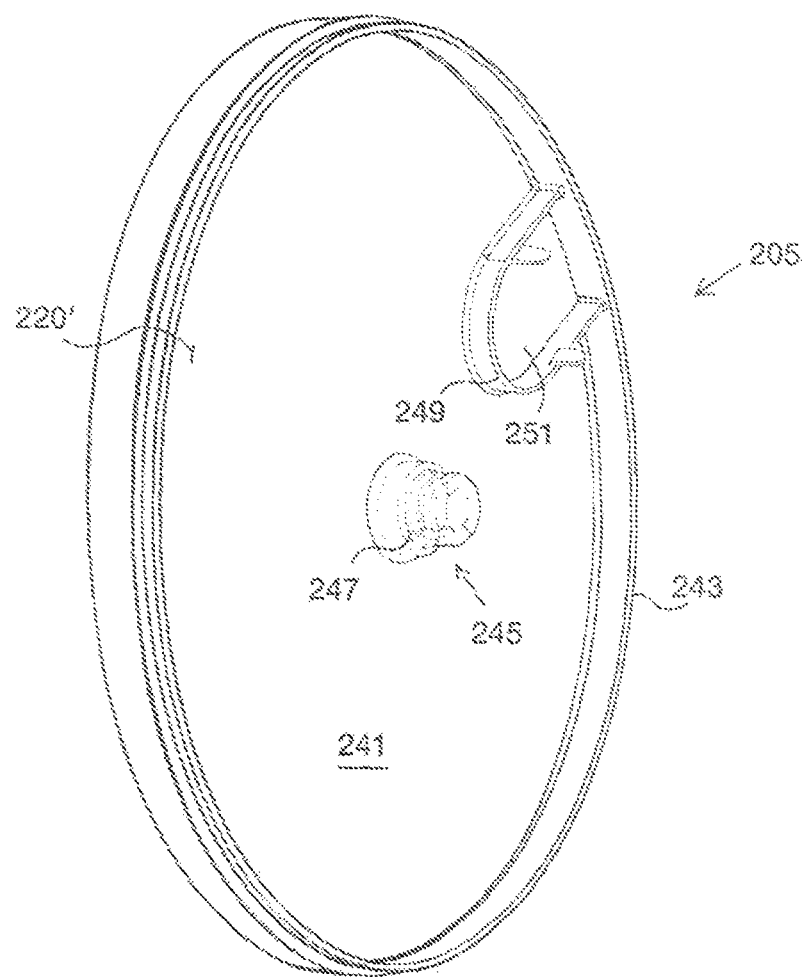
FIG. 8a is a perspective view of an alternative level element of a device according to the invention.
Figure 8C:
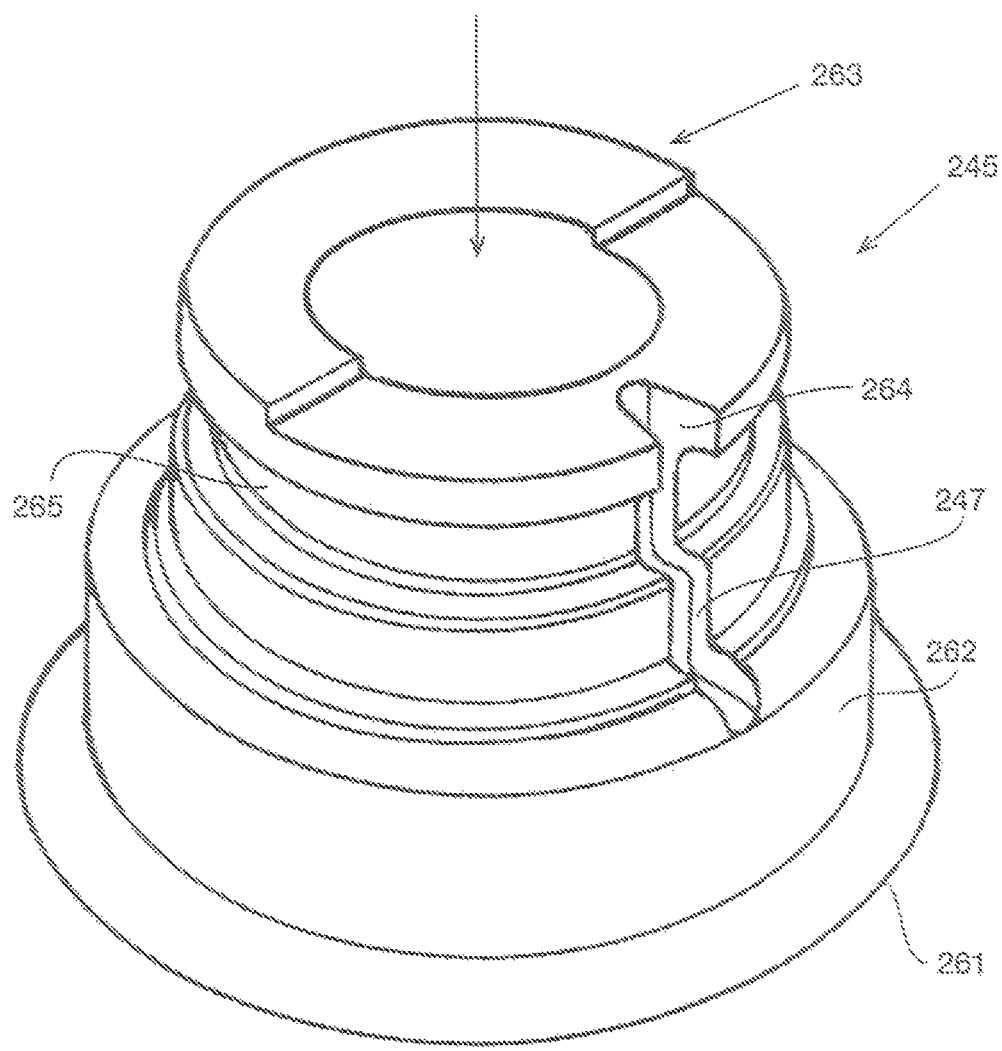

To achieve a reliable seal of the device 1, 101, 201 built up of parts to be connected by means of a connecting mechanism, it may be desirable to additionally affix a tape to the outer side of the parts of the device that are to be connected together. FIGS. 8a and 8b show in perspective view and vertical sectional view, respectively, of an alternative embodiment of a level element 205 according to the present invention. The level element 205 comprises an intermediate bottom 241 and an intermediate side wall 243 extending cylindrically relative to the intermediate bottom 241, which defines an intermediate space 220' of an interior (not shown in FIG. 8a) of an assembled device. The intermediate bottom 241 is provided with a U-shaped intermediate wall 249, which bounds a passage opening 251, and a passage 245 which can be connected to a supply channel (not shown) of a cover or to a correspondingly configured passage so as to form a passageway for fluid. The passage 245 has only one feed-through aperture 247, which is present in the end remote from the passage opening 251 of the wall of the passage 245, viz. in the extension of a line through the central axes of the passage channel and the passageway. The passage 245 is shown in more detail in FIG. 8c.

The passage 245 is circular in cross-section and has a flanged edge 261 at the bottom side, from which a first cylindrical wall 262 extends in a slightly converging manner. From there the wall of the passage 245 extends further upwards in slightly inwardly oriented steps. Disposed at the upper side is an annular edge 263, which is thicker on the side facing the passage channel (see FIG. 8a) than on the side remote from the passage channel. On the latter, thinner side a recess 264 is provided in the annular edge 263, which recess extends further downwards in the wall of the feed-through aperture 245 up to the cylindrical wall 262. The recess 264 and the extension thereof in the direction of the cylindrical wall 262 form a feed-through channel 247 for fluid. In use, a rubber ring functioning as a gasket is provided around a recessed wall portion 265 disposed directly below the annular edge 263. When two level elements 205 are stacked one on top of the other, the gasket of the lower passage sealingly abuts against the cylindrical wall 262 of the level element 205 stacked on top thereof. Thus, a passageway is formed by stacked-together hollow passages 245, wherein fluid flowing through the passageway under pressure can flow into the intermediate space 220' via the narrowed portion of the annular edge 263 and the feed-through aperture 247.

Figure 9B:
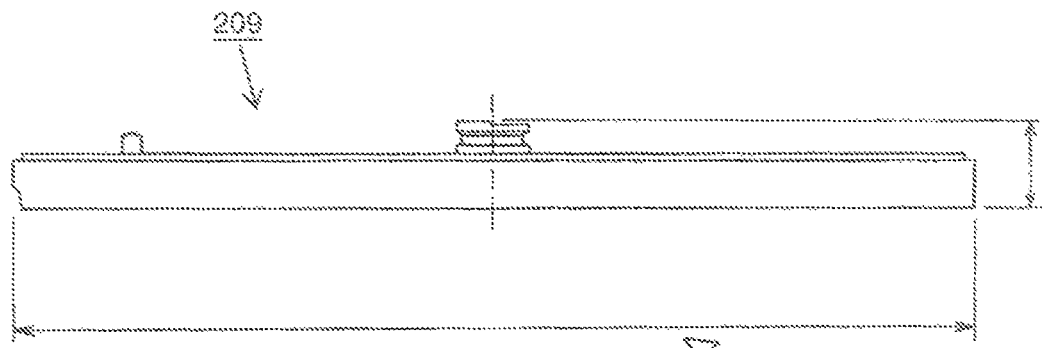
Figure 9A:
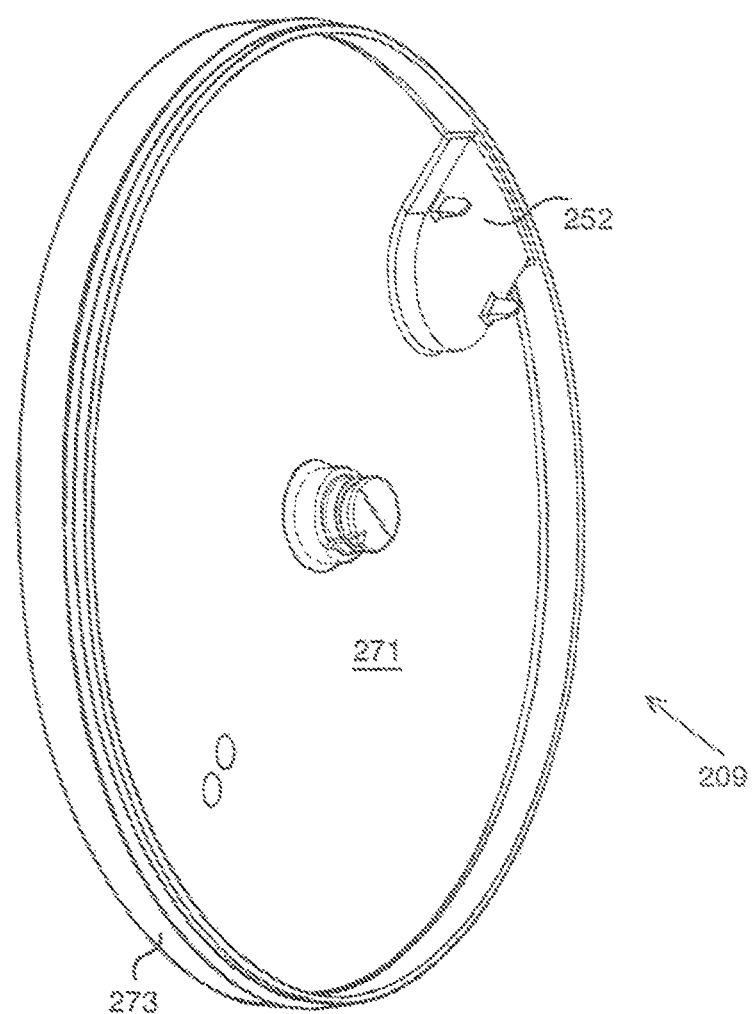
FIG. 9a is a perspective view of an alternative bottom part of a device according to the invention.
Figure 9C:
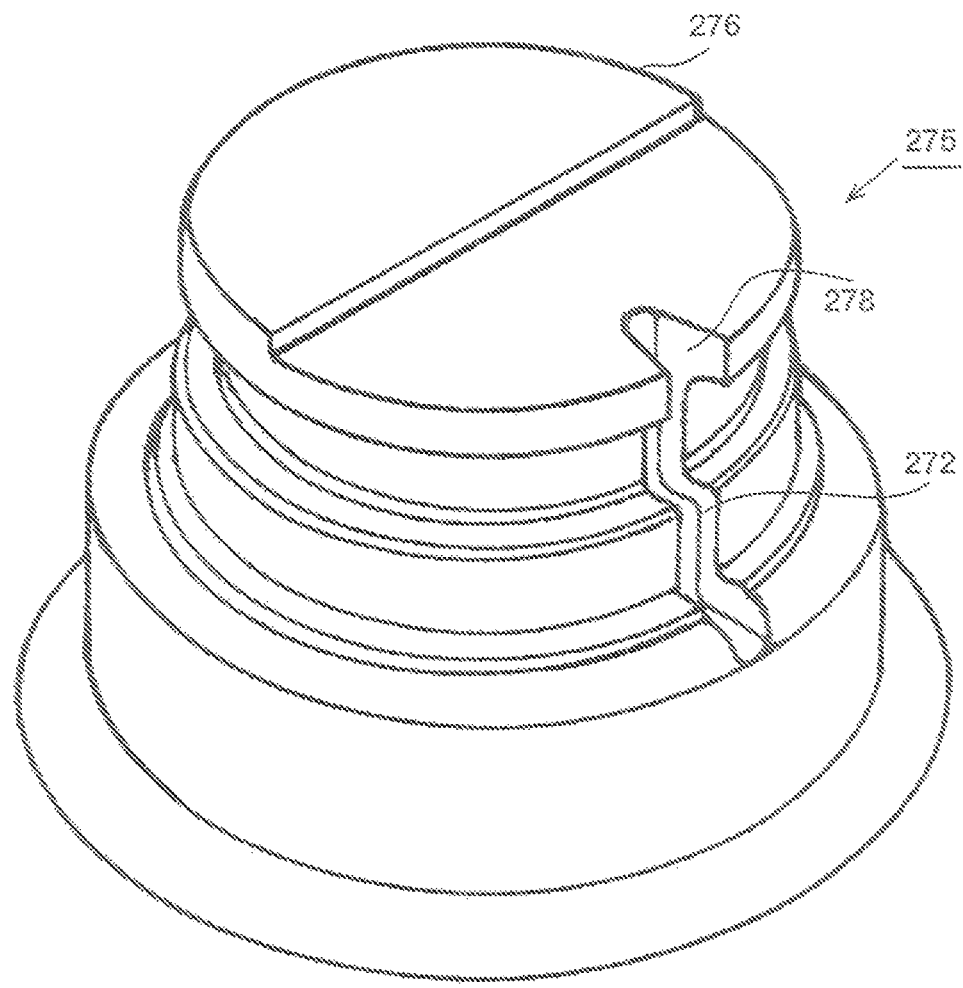

FIGS. 9a and 9b show in perspective view and vertical sectional view, respectively, a bottom part 209 that fits an alternative level element according to FIG. 8a. The bottom part 209 comprises a circular bottom wall 271, on the circumference of which a side wall extending transversely thereto is located. The side wall 273 extends cylindrically relative to the bottom wall 271. The bottom wall 271 comprises a bottom connecting part 275, which can be connected to a passage 245 of a level element 205 disposed thereabove. The bottom part 209 corresponds in large measure with the level element 205, but it comprises a closed elevated portion 252 instead of a passage opening 251 and a bottom connecting part 275 instead of a passage 245. The bottom connecting part 275 corresponds to the passage 245, with this difference that a circular plate element 276 having a relatively thick half and a relatively thin half is provided instead of the annular edge 263 provided with a thicker portion and a thinner portion. The relatively thin half is in turn provided with a recess 278, which merges in downward direction into a feed-through aperture 272. In use, the circular plate element 276 closes the passageway at the bottom side, while the feed-through aperture 272 allows fluid to flow into the intermediate space of the bottom part 209.

FIG. 10 shows a vertical sectional view of an assembly of a bottom part 209 with three level elements 205 and a cover according to the present invention. Similarly to the cover 3, the cover 203 is provided with a supply channel 215 for supplying fluid into the interior of the assembly, a discharge channel 227 for discharging fluid from the interior of the device 201 and an inlet and outlet opening 221 for supplying and discharging culture material. In use, a fluid line (not shown) is connected to each of the inlet 215 and outlet 227, whilst a line for liquid culture material is connected to the inlet and outlet opening 221. After the device 201 has been filled with culture material, in a comparable manner as described with reference to the first embodiment of the present invention, fluid is introduced under pressure into the passageway 245' via the supply channel 215. As a result of the relative overpressure relative to the internal volume made up of subvolumes 20', the fluid flows from the passageway 245' to the subvolumes 20' via the lowered portions of the annular walls 263 and the lowered portion of the annular plate element 276, respectively, into the respective feed-through apertures 247, 272. Because the feed-through apertures 247, 272 face away from the passage openings 251, the fluid will first flow in the direction of the part of the side wall 243, 273, respectively, remote from the passage openings 251 before flowing to the passage opening 251 in question. Because the U-shaped wall 249 extends less far upwards than the respective side walls 243, 273 of the level elements and the bottom part, respectively, the fluid can flow into the passage channel 251' from the subvolumes 20'. Because the inlet and outlet opening 221 is closed by means of a cap or by means of a hose in use, the fluid will flow through the passage channel 251' into the upper subvolume 20' at the upper side and subsequently out of the assembly 201 through the discharge channel 227. Thus, a very good distribution of the fluid over the respective subvolumes 20' is achieved, so that optimum conditions are generated for cultures present on the bottoms of the level elements and the bottom part.

In the second embodiment according to the present invention, two feed-through apertures may be provided for each level element or bottom part instead of one feed-through aperture 247, 272, respectively. The feed-through apertures will in that case be provided on either side of the position of the one feed-through aperture 247, 272 shown in FIGS. 8a-9c, staggered by 5° to at most 30°, in a passage 245 and a connecting part 275, respectively. Such positioning on the one hand provides a good distribution of the fluid over a subvolume and on the other hand prevents undesirable swirling of fluid within the subspace in question.

Although this is not shown in the figures, it is furthermore possible to make the bottom part, the level elements and the cover in the form of an upper wall in one part. In the case of a one-part device, the bottom connecting part is not necessary and a nozzle (not shown) connected to the supply channel for supplying the fluid to the culture on the bottom wall will suffice. It is also possible to provide a device that does not comprise levels, but only a single internal volume bounded by the upper wall, possibly configured as a cover, the side wall and the bottom wall.

It is also possible to implement the inventive concept in a device that comprises corners instead of using the cylindrical device shown in the figures.

The exemplary embodiments shown in the figures and described herein do not have any limitative effect on the scope of the present invention as defined in the appended claims. Many variants, which may or may not obvious to the skilled person, are conceivable within said scope of protection. The supply channel and the discharge channel for fluid are shown as lengths of pipe that project above the cover, but they may also be configured as through holes in the cover. The supply channel and the passageway may be provided slightly off-centre, i.e. staggered relative to the central axis of the device. Although only one feed-through is provided in the wall between the passageway and a respective subspace, it would also be conceivable to use two feed-throughs.

The invention claimed is:

1. A device for culturing cells, which device comprises a bottom wall, at least one side wall as well as an upper wall for forming an interior volume that is configured to be shut off from the outside world,
   a liquid culture comprising cells being present on the bottom wall in use, enclosed by said at least one side wall,
   at least one supply channel comprising a supply channel opening disposed in the upper wall, and at least one discharge channel disposed in the upper wall, wherein the at least one supply channel is configured to supply gas to the liquid culture and wherein the at least one discharge channel is configured to discharge gas wherein the at least one supply channel and the at least one discharge channel are separate channels, wherein the at least one supply channel is spaced from a central axis of the device by a distance which is smaller than half the smallest distance between the central axis and the at least one side wall or coincides with the central axis, and wherein said at least one supply channel and said at least one discharge channel are configured to distribute gas evenly throughout said device; and
   wherein the upper wall is further provided with at least one inlet and/or one outlet opening separate from the at least one supply channel and the at least one discharge channel and in addition to the at least one supply channel and the at least one discharge channel for supplying and/or discharging culture medium to and from, respectively, the interior volume; and
   wherein at least one intermediate bottom with at least one intermediate side wall is provided between the bottom wall and the upper wall, providing at least one intermediate space, in which the at least one intermediate space configured to hold another liquid culture with cells on the intermediate bottom in use, enclosed by the at least one intermediate wall, wherein the at least one intermediate bottom further includes an intermediate wall defining a passage having a fluid inlet aperture and a fluid outlet aperture, at least a portion of the intermediate wall is in fluid communication with the supply channel opening, wherein said at least one intermediate bottom is in fluid communication with said at least one supply channel via said passage for fluid flow in a direction of the bottom wall, and wherein said intermediate wall further comprises at least one feed-through aperture in fluid communication with the passage for supplying fluid into the at least one intermediate space in a connected condition.

2. The device according to claim 1, wherein the at least one supply channel is spaced from the central axis of the device by a distance which is smaller than a quarter of the smallest distance between the central axis and the at least one side wall.

3. The device according to claim 1, wherein the upper wall is a cover, whilst the bottom wall is provided with a bottom connecting part configured to be connected to, in the cover or the at least one intermedia bottom, wherein the bottom connecting part comprises one or more feedthrough apertures for allowing fluid to pass into interior volume in a connected condition.

4. The device according to claim 1, wherein the at least one intermediate bottom can be detachably connected to another intermediate side wall or to the at least one side wall by means of a connecting mechanism.

5. The device according to claim 4, wherein the connecting mechanism is made up of an end portion of a bottom connecting part as well as an end portion of the intermediate wall of the at least one intermediate bottom, wherein each end portion is configured so that it can be connected in the supply channel opening of the at least one supply channel of the upper wall, the end portion of the bottom connecting part can be connected in the fluid outlet aperture of the intermediate wall, wherein the end portion of the bottom connecting part or the at least one supply channel opening is provided with at most two feed-through apertures through which fluid can be supplied to each culture in the device in a connected condition, and wherein said at least one through-aperture of the intermediate wall is provided at the end portion of the intermediate and includes at most two-feed through apertures through which fluid can be supplied to each culture in the device in a connected condition.

6. The device according to claim 4, wherein the connecting mechanism is further provided with a stepped upper edge of the at least one side wall and/or the intermediate side wall remote from the bottom wall or the at least one intermediate bottom as well as with a complementarily stepped upper wall edge of the upper wall and/or with a complementarily stepped edge of the at least one intermediate bottom.

7. The device according to claim 6, wherein the connecting mechanism is further provided with a snap mechanism comprising at least one cam and at least one notch in the upper wall edge and/or the edge of the at least one intermediate bottom and also in the upper edge of the at least one side wall and/or at least one intermediate side wall.

8. The device according to claim 4, wherein the connecting mechanism is provided with at least two fingers pointing in the direction of the bottom wall, which fingers are each attached with one end thereof to a side of the upper wall and/or the at least one intermediate bottom that faces the bottom wall, and which are arranged around the at least one supply channel and/or said intermediate wall and which are fixed in recesses when said connecting mechanism is engaged.

9. The device according to claim 8, wherein the connecting mechanism comprises a bottom connecting part, and wherein the bottom connecting part and/or the intermediate wall is/are provided with recesses that cooperate with the at least two fingers.

10. The device according to claim 8, wherein a part of the bottom connecting part and at least one passage under the end portion of the bottom connecting part is conical in shape, which conical part is further provided with radially extending flanges.

11. The device according to claim 1, characterised in that the at least one inlet and/or outlet opening is disposed decentrally relative to the upper wall, with the decentrally disposed inlet and/or outlet opening being spaced from the central axis of the device by a distance larger than half the smallest distance between the central axis and the at least one side wall.

12. The device according to claim 1, characterised in that at least one inlet and/or outlet opening is located adjacent to the side wall of the device.

13. The device according to claim 1, wherein the central axes of the inlet and/or outlet opening, the at least one supply channel as well as the discharge channel lie in a virtual plane, which virtual plane extends transversely to the upper wall.

14. The device according to claim 1, wherein said at least one intermediate bottom includes a plurality of intermediate bottoms,
characterised in that a passage opening is provided in each of said plurality of intermediate bottoms, which passage openings are aligned with said at least one inlet and/or outlet opening in the upper wall so as to form a passage channel for culture liquid.

15. The device according to claim 14, characterised in that each of said passage openings is bounded by a second intermediate wall that extends perpendicularly to the intermediate bottom wall, such that the passage channel is in communication with the respective interior space.

16. The device according to claim 1, wherein the bottom wall is provided with at least one sensor cavity for a sensor.

17. The device according to claim 1, wherein the device has a cylindrical configuration.

18. The device according to claim 14, wherein the passage is hollow so as to provide a passageway in a connected condition, wherein the bottom connecting part has an upper side which, in a connected condition, forms the end point of the passageway.

19. The device according to claim 18, wherein the passage and the bottom connecting part are configured identically.

20. The device according to claim 1, wherein the fluid can be supplied to the culture on the bottom wall by means of a nozzle connected to at least one supply channel.

21. The device according to claim 1, characterised in that the height of the at least one intermediate side wall ranges between 4-10 mm.

22. A perfusion system for supplying and discharging liquid to and from a device for culturing cells, which perfusion system comprises a device according to claim 1, a supply reservoir as well as an outlet, wherein the device is provided with a supply line for supplying liquid to the interior of the device, as well as a discharge line spaced from the supply line for discharging liquid from the interior of the device, wherein the supply line as well as the discharge line are in the bottom wall and can be connected to the supply reservoir and the outlet, respectively, by means of hoses.

23. The device according to claim 1, characterised in that exactly one feed-through aperture is provided in said intermediate wall.

24. The device according to claim 1, wherein the upper wall is a cover, whilst the bottom wall is provided with a bottom connecting part configured to be connected to the supply channel opening of the at least one supply channel of the upper wall, wherein the supply channel opening comprises one or more feed-through apertures for allowing fluid to pass into the interior in a connected condition.

25. The device according to claim 18, characterised in that the proportion between a cross-section of the passage channel and that of the passageway is greater than 2:1.

* * * * *